United States Patent [19]

Uesugi et al.

[11] Patent Number: 5,139,740
[45] Date of Patent: Aug. 18, 1992

[54] POLYPRENYL COMPOUND COMPOSITION FOR SOFT CAPSULES

[75] Inventors: Keizo Uesugi, Aichi; Masanori Kayano, Gifu, both of Japan

[73] Assignee: Eisai Co., Ltd., Tokyo, Japan

[21] Appl. No.: 546,084

[22] Filed: Jun. 29, 1990

[30] Foreign Application Priority Data

Jul. 10, 1989 [JP] Japan .................. 1-177324

[51] Int. Cl.$^5$ .................................................. A61K 9/48
[52] U.S. Cl. .................................... 424/451; 424/456; 424/455; 514/412
[58] Field of Search ................... 424/455, 456, 451; 514/412

[56] References Cited

U.S. PATENT DOCUMENTS 4,727,109  2/1988  Schmidt et al. ............... 424/456

Primary Examiner—Thurman K. Page
Assistant Examiner—Leon R. Horne
Attorney, Agent, or Firm—Flynn, Thiel, Boutell & Tanis

[57] ABSTRACT

A pharmacological composition for soft capsules, containing a polyprenyl compound having the formula (1) and a surfactant and/or an unsaturated aliphatic acid, has improved absorbability.

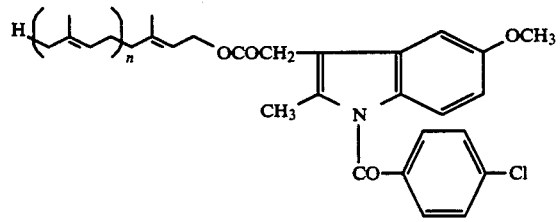

wherein n represents 1 to 3.

18 Claims, No Drawings

POLYPRENYL COMPOUND COMPOSITION FOR SOFT CAPSULES

The invention relates to a pharmacological polyprenyl compound composition for soft capsules having improved in view of absorbability of the pharmacological ingredient.

PRIOR ART

Polyprenyl compounds of the general formula (I):

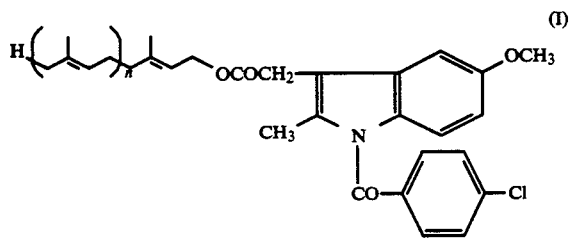

wherein n represents 1 to 3, were developed as the prodrug of indomethacin. They have a low toxicity and a remarkable anti-inflammatory effect.

It has been reported that non-steroidal compounds such as indometacin clinically exhibited various adverse reactions such as gastrointestinal or renal disturbances.

7:3(2E:2Z)geometric mixture of (6E)-3,7,11-trimethyl-2,6,10-dodecatrienyl 1-(p-chlorobenzoyl)-5-methoxy-2-methyl-1H-indole-3-acetate, called indomethacin farnesyl, which is one of the compounds having the formula (1) and used as the prodrug of indomethacin, is known as a long-lasting antiinflammatory medicine exhibiting only slight adverse reactions. It is disclosed in JP-A 58-15940.

Capsules having a high polyprenyl compound content are clinically necessary. When a fat-soluble drug is to be filled in a hard capsule, a capsule of a large size is necessary since the volume of the contents is increased by the formulation. Thus problems are posed when such a large capsule is taken by the patient.

It is known that the absorption of fat-soluble drugs through the intestinal tract is influenced by the functions of the liver and pancreas and that they are hardly absorbed, particularly when no bile is secreted [see Gall Torres, H. E., Lipids, 5, 379 (1970)].

Thus, the absorption of the fat-soluble drugs through the intestinal tract is different among individuals depending on the function of secreting of the digestive juice. Generally, the absorption of the fat-soluble drugs is apt to be influenced by the digestive functions of the living body and meals.

Some of the fat-soluble drugs are formulated in the form of soft capsules by using a vegetable oil as a solubilizer.

A composition comprising a polyprenyl compound and a vegetable oil still has poor absorbability.

It is known that a fat-soluble drug such as a polyprenyl compound combines with bile to form a mixed micelle, from which the drug is released and absorbed through the microvilli of the small intestine into the blood or lymphatic vessels.

In filling the fat-soluble drug into a soft capsule, a technique wherein the drug is dispersed in a liquid fat with a polyglycerol fatty acid ester to suitably the viscosity for filling was tried. Polyglycerol fatty acid esters have already been employed for the purpose of solubilizing fat-soluble vitamins (refer to, for example, the invention disclosed in U.S. Pat. No. 3,922,634).

Japanese Patent Laid-Open No. 13508/1983 discloses a technique wherein a polyglyceride is incorporated into a composition of a fat soluble drug for the purpose of improving the absorption of this drug and facilitating the administration of the drug.

In the investigations of the formulation of fat-soluble drugs, the inventors have investigated the self-emulsifiable type and micelle-forming type as will be understood from their absorption route.

SUMMARY OF THE INVENTION

The pharmacological composition for soft capsules, according to the invention, comprises a polyprenyl compound having the formula (1) and a surfactant and/or an unsaturated aliphatic acid, having improved absorbability.

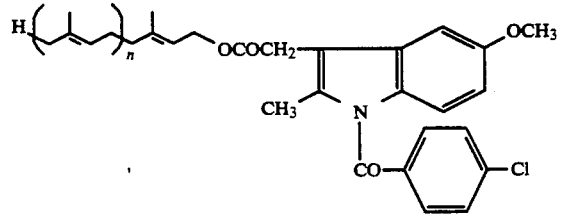

wherein n represents 1 to 3,

It is preferable that the polyprenyl compound is 7:3(2E:2Z)geometric mixture of (6E)-3,7,11-trimethyl-2,6,10-dodecatrienyl 1-(p-chlorobenzoyl)-5-methoxy-2-methyl-1H-indole-3-acetate, called indomethacin farnesyl. The surfactant may be selected from polyoxyethylenepolyoxypropylene glycol and polyoxyethylene hardened castor oil. The unsaturated aliphatic acid may be selected from oleic acid, linoleic acid and linolenic acid. Polyoxyethylene(160)polyoxypropylene(30) glycol is most preferable, having 160 oxyethylene units and 30 oxypropylene units on the average. Polyoxyethylene(40-60) hardened castor oil is also more preferable, having 40 to 60 oxyethylene units on the average. Polyoxyethylene(40) hardened castor oil is also most preferable.

The following three compositions are preferable: A composition comprising indomethacin farnesyl and polyoxyethylene(160)polyoxypropylene(30) glycol a composition comprising indomethacin farnesyl and polyoxyethylene(40-60) hardened castor oil and a third composition comprising indomethacin farnesyl, polyoxyethylene(160)polyoxypropylene(30) glycol and polyoxyethylene(40-60) hardened castor oil.

The polyoxyethylene hardened castor oil may be called polyoxyethylene hydrogenated castor oil. Rat lymph absorption and beagle absorption tests were conducted.

In the rat lymph absorption test, Pluronic F 68®, polyoxyethylene(60)-harden monoglycerol fatty acid ester or linolic acid was used for the formulation. In this test, 5 mg/kg of indometacin farnesyl was orally administered to SD rats (12-week old) and indometacin farnesyl in the lymphatic vessels was determined according to HPLC by the lymph cannulation method.

In the beagle absorption test, Pluronic F 68®, polyoxyethylene(60)-hardened castor oil, propylene glycol dicaprylate, cotton seed oil, medium-chain fatty acid triglyceride, or an unsaturated fatty acid such as oleic acid, linolic acid or linolenic acid was used for the formulation to examine the absorbability.

In this test, the crossover method was employed by using six female beagles with the administration of 200 mg of indometacin farnesyl orally to each of them 30 min after breakfast, and sampling their blood at intervals to determine the concentration of indometacin farnesyl in their blood according to HPLC.

In the rat lymph absorption test and beagle absorption test, particularly excellent absorption was exhibited by Pluronic F 68®, polyoxyethylene(60)-hardened castor oil, oleic acid, linolic acid, linolenic acid, etc.

As a result of the above-described investigations, it has been found that the absorption of a polyprenyl compound can be accelerated by a pharmaceutical means where the polyprenyl compound is combined, with one or more compounds selected from among polyoxyethylene polyoxypropylene glycol, polyoxyethylene-hardened castor oil, oleic acid, linolic acid and linolenic acid and then encapsulated to form soft capsules. The present invention has been completed on the basis of this finding.

Thus, the present invention provides a process for producing soft capsules having a high content of a polyprenyl compound of the above general formula (I), characterized in that one or more substances selected from the group consisting of polyoxyethylene polyoxypropylene glycol, polyoxyethylene-hardened castor oil, oleic acid, linolic acid and linolenic acid are incorporated thereinto.

The relative amount of the one or more substances selected from among polyoxyethylene polyoxypropylene glycol, polyoxyethylene-hardened castor oil, oleic acid, linolic acid and linolenic acid is preferably 0.1 to 1 part by weight, still preferably 0.3 to 0.5 part by weight, per part by weight of the polyprenyl compound.

The polyoxyethylene polyoxypropylene glycol used in the present invention, which is produced by the addition polymerization of ethylene oxide with polypropylene glycol obtained by the, addition polymerization of propylene oxide with water, is represented by the formula:

$$HO(C_2H_4O)_n(C_3H_6O)_m(C_2H_4O)_n.H$$

It has average degrees of polymerization of propylene oxide and ethylene oxide of about 21 and 22, about 39 and 54, about 39 and 124 or about 30 and 160, respectively. Particularly preferred is Pluronic F 68®, i.e. polyoxyethylene(160) polyoxypropylene(30) glycol having average degrees of polymerization of propylene oxide and ethylene oxide of about 30 and about 160, respectively.

The polyoxyethylene-hardened castor oil used in the present invention is a nonionic surfactant having an average number of ethylene oxide molecules added of about 40, 50 or 60, which is produced by the addition polymerization of ethylene oxide with a hardened oil obtained by hydrogenating castor oil. Particularly preferred is polyoxyethylene(60)-hardened castor oil.

In the present invention, known additives used in the production of soft capsules can be used in addition to the above-described indispensable components.

The soft capsules can be produced by a known soft capsule producing machine.

EXAMPLES

The following Examples will further illustrate the present invention but by no means limit the invention.

EXAMPLE 1

200 g of indomethacin farnesyl, 0.3 g of dl-alpha-tocopherol, 30 g of an aliphatic glyceride, 50 g of an ester of propylene glycol and an aliphatic acid were mixed with 60 g of polyoxyethylene(160)polyoxypropylene(30)glycol[(Pluronic F68 tradename), and 4.7 g of light anhydrous silicic acid. The mixture was stirred at 60 degree C for 30minutes to obtain an uniform composition. It was then allowed to cool down to room temperature. Soft capsules of 345 mg/cap were charged with the composition, by a continuous automatic soft capsule producing machine of the punching type, available from Leinen & Sons Co., Ltd. and equipped with capsule mold Oval 7.5.

EXAMPLE 2

200 g of indomethacin farnesyl, 0.3 g of dl-alpha-tocopherol, 29.7 g of an aliphatic glyceride, 55 g of an ester of propylene glycol and an aliphatic acid were mixed with 60 g of polyoxyethylene hydrogenated castor oil 60. The mixture was stirred at 60 degree C for 30 minutes to obtain an uniform composition. It was then allowed to cool down to room temperature. Soft capsules of 345 mg/cap were obtained in the same way as shown in Example 1.

EXAMPLE 3

200 g of indomethacin farnesyl, 0.3 g of dl-alpha-tocopherol and 100 g of an aliphatic glyceride were mixed with 59.7 g of oleic acid. The mixture was stirred at 60 degree C for 15 minutes to obtain an uniform composition. It was then allowed to cool down to room temperature. Soft capsules of 360 mg/cap were obtained in the same way as shown in Example 1.

Comparative Example 1

200 g of indomethacin farnesyl, 0.3 g of dl-alpha-tocopherol, 100 g of an aliphatic glyceride and 59.7 g of cotton seed oil were mixed with each other. The mixture was stirred at 60 degree C for 30 minutes to obtain an uniform composition. It was then allowed to cool down to room temperature. Soft capsules of 360 mg/cap were obtained in the same way as shown in Example 1.

Comparative Example 2

200 g of indomethacin farnesyl 0.3 g of dl-alpha-tocopherol, 100 g of an aliphatic glyceride and 59.7 g of middle chain aliphatic triglycerides were mixed with each other. The mixture was stirred at 60 degree C for 30 minutes to obtain an uniform composition. It was then allowed to cool down to room temperature. Soft capsules of 360 mg/cap were obtained in the same way as shown in Example 1.

Comparative Example 3

200 g of indomethacin farnesyl, 60 g of an aliphatic ester of propylene glycol and 5 g of sorbitan aliphatic acid ester were mixed with each other. The mixture was stirred at 60 degree C for 30 minutes to obtain an uniform composition. It was then allowed to cool down to room temperature. Soft capsules of 265 mg/cap were obtained in the same way as shown in Example 1.

Administration test

Beagle dogs were orally administered with the capsules obtained in Examples 1 to 3 and then Comparative examples 1 to 3, respectively, to observe the absorption of indomethacin farnesyl. Results are shown in Table 1.

Method

Six female beagles were used to determine indometacin farnesyl in the blood by the crossover method.

In the test, each sample was orally administered 30 min after breakfast and 2.5 ml of blood was sampled at intervals to determine the concentration of indometacin farnesyl under the HPLC conditions which will be described below.

The maximum blood concentration, $C_{max}$ (μg/ml), and the area under the blood concentration-time curve, AUC (μg hr/ml), 6 h after the administration of each of samples A to F were determined and expressed in terms of relative value with respect to those of a standard formulation.

HPLC Conditions stationary phase: Nucleosil ®10C18, 4.6 mm diameter × 150 mm
mobile phase: methanol/water (300/16)
flow rate: 1 ml/min
detection: UV$_{260\ nm}$

TABLE 1

| | Cmax | AUS$_0^6$ |
|---|---|---|
| Example | | |
| 1 | 1.97 | 1.42 |
| 2 | 1.79 | 1.45 |
| 3 | 2.04 | 1.62 |
| Comparative Example | | |
| 1 | 1.34 | 0.96 |
| 2 | 1.37 | 1.15 |
| 3 | 1 | 1 |

We claim:

1. A pharmacological composition for soft capsules, comprising a polyprenyl compound having the formula (1) and a surfactant and/or an unsaturated aliphatic acid

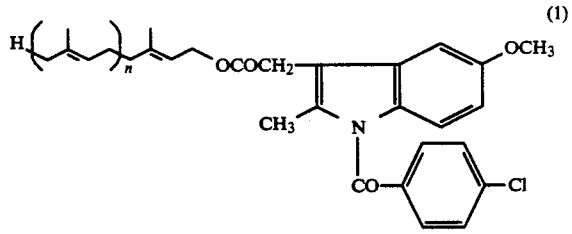

wherein n represents 1 to 3.

2. The composition as claimed in claim 1, in which said polyprenyl compound is indomethacin farnesyl.

3. The composition as claimed in claim 1, in which said surfactant is selected from the group consisting of polyoxyethylenepolyoxypropylene glycol and polyoxyethylene hardened castor oil.

4. The compositon as claimed in claim 1, in which said unsaturated aliphatic acid is selected from the group consisting of oleic acid, linoleic acid and linolenic acid.

5. The composition as claimed in claim 1, in which said surfactant is polyoxyethylene (160)polyoxypropylene(30) glycol.

6. The composition as claimed in claim 1, in which said surfactant is polyoxyethylene(40-60) hardened castor oil.

7. The compositon as claimed in claim 1, which comprises indomethacin farnesyl and polyoxyethylene(160-)polyoxypropylene(30)glycol.

8. The compositon as claimed in claim 1, which comprises indomethacin farnesyl and polyoxyethylene(40-60) hardened castor oil.

9. The composition as claimed in claim 1, which comprises indomethacin farnesyl, polyoxyethylene(160-)polyoxypropylene(30) glycol and polyoxyethylene(40-60) hardened castor oil.

10. A pharmacological composition for soft capsules having improved absorbability, consisting essentially of a polyprenyl compound having the formula (1) and a surfactant and/or an unsaturated aliphatic acid

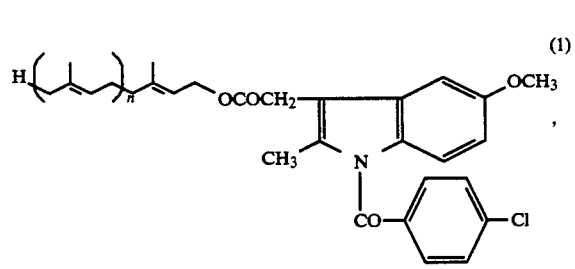

wherein n represents 1 to 3.

11. The compositon as claimed in claim 10, in which said polyprenyl compound is indomethacin farnesyl.

12. The compositon as claimed in claim 10, in which said surfactant is selected from the group consisting of polyoxyethylenepolyoxypropylene glycol and polyoxyethylene hardened castor oil.

13. The composition as claimed in claim 10, in which said unsaturated aliphatic acid is selected from the group consisting of oleic acid, linoleic acid and linolenic acid.

14. The composition as claimed in claim 10, in which said surfactant is polyoxyethylene(160)polyoxypropylene(30) glycol.

15. The composition as claimed in claim 10, in which said surfactant is polyoxyethylene(40-60) hardened castor oil.

16. The composition as claimed in claim 10, which consists essentially of indomethacin farnesyl and polyoxyethylene(160)-polyoxypropylene(30)glycol.

17. The composition as claimed in claim 10, which consists essentially of indomethacin farnesyl and polyoxyethylene(40-60) hardened castor oil.

18. The compositon as claimed in claim 10, which consists essentially of indomethacin farnesyl, polyoxyethylene(160)-polyoxypropylene(30) glycol and polyoxyethylene(40-60) hardened castor oil.

* * * * *